(12) United States Patent
Caldwell et al.

(10) Patent No.: US 10,869,722 B2
(45) Date of Patent: Dec. 22, 2020

(54) METHOD AND FIXTURE FOR GUIDED PEDICLE SCREW PLACEMENT

(71) Applicants: Michael R. Caldwell, Rochester, NY (US); Mark W. Olles, Hilton, NY (US); Amit Singla, Cedar Falls, IA (US)

(72) Inventors: Michael R. Caldwell, Rochester, NY (US); Mark W. Olles, Hilton, NY (US); Amit Singla, Cedar Falls, IA (US)

(73) Assignee: Rochester Institute of Technology, Rochester, NY (US)

( * ) Notice: Subject to any disclaimer, the term of this patent is extended or adjusted under 35 U.S.C. 154(b) by 0 days.

(21) Appl. No.: 15/801,975

(22) Filed: Nov. 2, 2017

(65) Prior Publication Data

US 2018/0116727 A1    May 3, 2018

Related U.S. Application Data

(60) Provisional application No. 62/416,474, filed on Nov. 2, 2016.

(51) Int. Cl.
| | |
|---|---|
| *A61B 34/10* | (2016.01) |
| *B33Y 80/00* | (2015.01) |
| *B33Y 50/02* | (2015.01) |
| *A61B 17/17* | (2006.01) |
| *G16H 50/50* | (2018.01) |
| *A61B 17/70* | (2006.01) |
| *G16H 20/40* | (2018.01) |
| *A61B 17/00* | (2006.01) |
| *A61B 17/56* | (2006.01) |

(52) U.S. Cl.
CPC .......... *A61B 34/10* (2016.02); *A61B 17/1757* (2013.01); *A61B 17/7043* (2013.01); *B33Y 50/02* (2014.12); *B33Y 80/00* (2014.12); *G16H 20/40* (2018.01); *G16H 50/50* (2018.01); *A61B 17/7032* (2013.01); *A61B 17/7037* (2013.01); *A61B 2017/00526* (2013.01); *A61B 2017/564* (2013.01); *A61B 2017/568* (2013.01); *A61B 2034/102* (2016.02); *A61B 2034/105* (2016.02); *A61B 2034/107* (2016.02); *A61B 2034/108* (2016.02)

(58) Field of Classification Search
CPC .............. A61B 34/10; A61B 2034/101; A61B 2034/102; A61B 2034/105; A61B 2034/107; A61B 2034/108
USPC ......................................... 606/86 A, 96, 279
See application file for complete search history.

(56) References Cited

U.S. PATENT DOCUMENTS

| | | |
|---|---|---|
| 6,932,842 B1 | 8/2005 | Litschko et al. |
| 8,175,683 B2 | 5/2012 | Roose |
| 8,298,235 B2 | 10/2012 | Grinberg et al. |

(Continued)

FOREIGN PATENT DOCUMENTS

| | | |
|---|---|---|
| CN | 203915053 U | 11/2014 |
| CN | 104644258 | 5/2015 |

(Continued)

*Primary Examiner* — Eduardo C Robert
*Assistant Examiner* — Christina Negrellirodriguez
(74) *Attorney, Agent, or Firm* — Bond, Schoeneck & King, PLLC; Joseph Noto (57) ABSTRACT

A customized patient-specific combined template and implant for spinal fixation and method for use.

9 Claims, 13 Drawing Sheets

(56) References Cited

U.S. PATENT DOCUMENTS

| | | | |
|---|---|---|---|
| 8,298,237 | B2 | 10/2012 | Schoenefeld et al. |
| 8,486,150 | B2 | 7/2013 | White et al. |
| 8,641,721 | B2 | 2/2014 | Aram et al. |
| 8,758,357 | B2 | 6/2014 | Frey |
| 8,870,889 | B2 | 10/2014 | Frey |
| 9,198,678 | B2 | 12/2015 | Frey et al. |
| 9,295,497 | B2 | 3/2016 | Schoenefeld et al. |
| 9,480,504 | B1 | 11/2016 | Schafer et al. |
| 9,642,633 | B2 | 5/2017 | Frey et al. |
| 9,763,722 | B2 | 9/2017 | Roybal |
| 2012/0289965 | A1 | 11/2012 | Gelaude et al. |
| 2016/0030067 | A1* | 2/2016 | Frey .................. A61B 17/15 606/86 A |

FOREIGN PATENT DOCUMENTS

| | | |
|---|---|---|
| CN | 106137373 A | 11/2016 |
| CN | 106236256 A | 12/2016 |
| EP | 2502582 | 9/2012 |
| EP | 2749235 | 7/2014 |
| WO | 2017001851 A1 | 1/2017 |

\* cited by examiner

METHOD AND FIXTURE FOR GUIDED PEDICLE SCREW PLACEMENT

CROSS REFERENCE

This application claims the benefit of the filing date of U.S. Provisional Patent Application No. 62/416,474, filed Nov. 2, 2016, which is hereby incorporated by reference in its entirety.

FIELD

The present disclosure relates generally to customized patient-specific spinal fixation, and in particular to customized patient-specific combined template and implant and method for spinal fixation.

BACKGROUND

The traditional way of placing the pedicle screws is to use the anatomical landmarks which at many times can be a best guess resulting in breaches of the pedicle and causing neurological injuries. Additional modalities used include the intra-operative fluoroscopy, which results in radiation exposure and more intra-operative time. Moreover it only adds a little more certainty in placement of pedicle screws.

Figure 2:
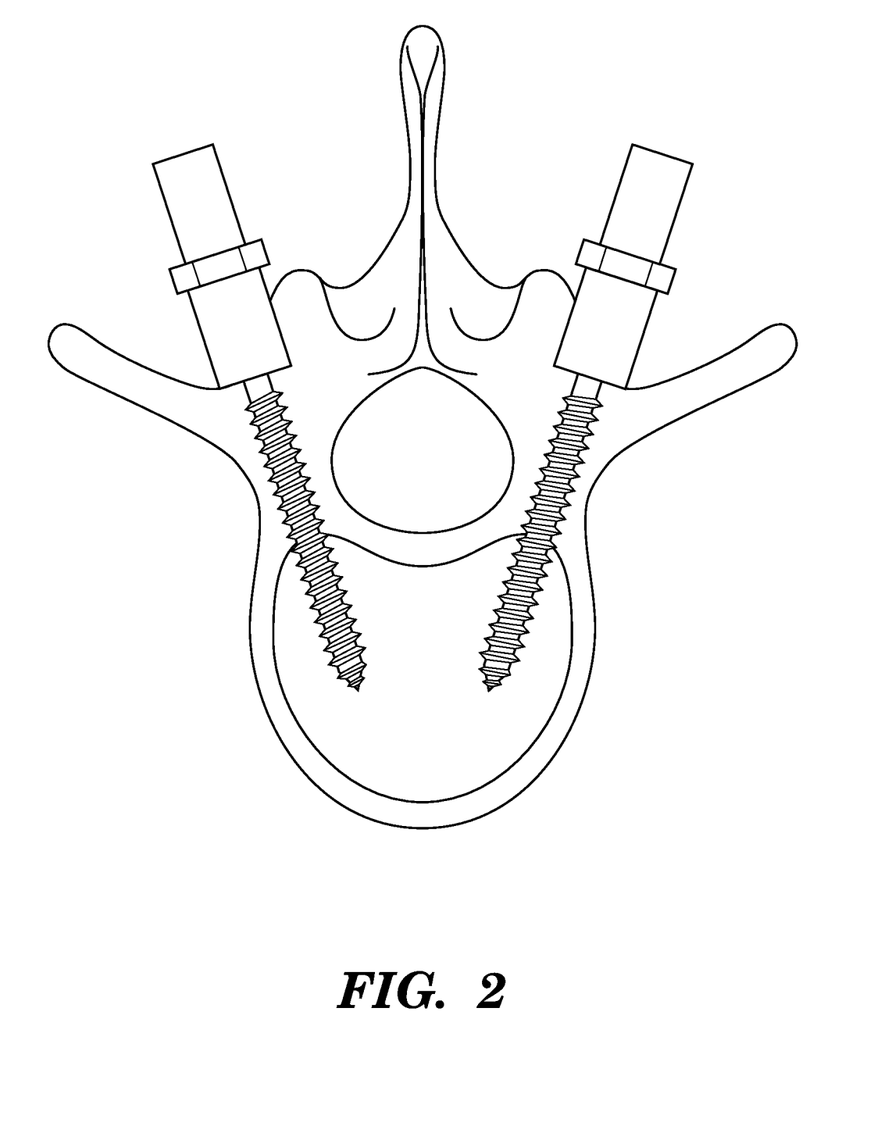
FIG. 2 is a top view of pedicle screws inserted into a vertebra in accordance with a prior art method.
Figure 3:
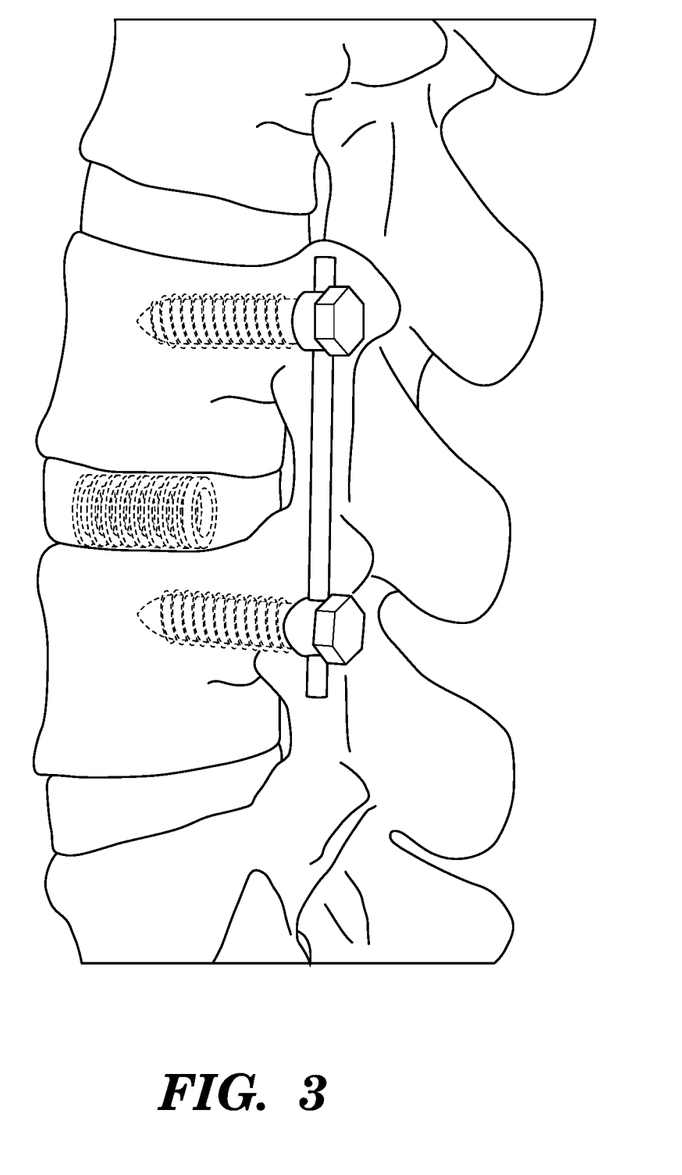
FIG. 3 is a side view of pedicle screws holding spinal alignment in accordance with a prior art method.

Current methods involve the placement of a series of screws with articulating heads through the pedicles in the vertebra that lie in the affected region of the spine, as shown in FIG. 2. Once the screws are placed a titanium rod is secured to the screws to prevent relative motion of adjacent vertebra, as shown in FIG. 3. Improper placement of a screw can cause damage to the vertebra, damage to surrounding nerves, spinal cord, paralysis, bowel and bladder problems, injury to large blood vessels resulting in significant hemorrhage which can be fatal or need for later operations to replace and correct damaged screws. Currently, most commonly the screws and rods are placed by hand relying on the skill and technique of the surgeon for optimal placement. Typically a device is used to inspect the passage after the trajectory for the screw is created, and fluoroscopy is performed post placement to verify screw location. Fluoroscopy can also be performed to choose the entry point for the screw trajectory and track it while the screw is placed through the pedicle. However, this necessitates significant amount of radiation and time and even then the rate of screw misplacement is quite high.

Other modalities tried and used include intra-operative navigation. This type of navigation includes; continuous fluoroscopy, image guided techniques requiring cameras and infra-red sensors, specialized instrumentation with directional sensors embedded into the device.

Secondary modalities include inspection after the screw trajectories are drilled, this includes; ultrasound inspection of the drilled area, as well as Electromyography while drilling the trajectories. This equipment is expensive and time-consuming. Many university or community based hospitals can't afford the navigation equipment.

Recent approaches have included the additive manufacturing of implantable titanium based cages that are developed to fit patient specific anatomy. Other approaches have included custom built fixtures to align the spine and aid in placement of screws or guides prior to the use of implantable fixtures.

SUMMARY

In accordance with one aspect of the present invention, there is provided a method for spinal fixation including scanning an affected segment of the spine of a patient in need of spinal fixation to generate image data; generating a 3D model of the spine from the image data; selecting a set of specific screw paths in the affected segment of the spine to best treat the patients' condition; using software to make a digital template for a fixture; modifying the digital template of the fixture to fit the selected screw paths; making the fixture from the finished digital template by additive manufacturing; locating the fixture on the affected segment of the spine; passing the drill through a drill guide and each screw passage in the fixture; removing the guide once the screw depth is verified; placing a standard surgical screw in a screw passage in the fixture and tightening the screw until the fixture boss is tightly seated to the vertebra; and repeating for each screw passage in the fixture.

In accordance with another aspect of the present disclosure, there is provided a customized patient-specific fixture for spinal fixation including a combination additive manufacturing-made fixture comprising a template comprising a plurality of screw passages in the fixture suitable for tightening a plurality of screw passage fixture bosses to the vertebra, and implant comprising self-alignment members, which fixture remains screwed on the vertebra after spinal fixation.

These and other aspects of the present disclosure will become apparent upon a review of the following detailed description and the claims appended thereto.

DETAILED DESCRIPTION

The device is a single rigid component that is developed to fit the curvature and specific features of the patient in whom it will be used. The device acts as a guide for drilling the trajectories and for subsequent placement of screws in vertebra, with the intention to correct and/or prevent issues related to the spine. The device also acts as a permanent fixture remaining attached to the spine to provide support and/or stability. The device is composed of biologically compatible materials; examples include but are not limited to titanium alloys, cobalt chromium and molybdenum steels. The device is built to match the specific geometry and locations of each patient. The device uses anatomical locations on the patients' vertebra to locate and align.

Figure 1:
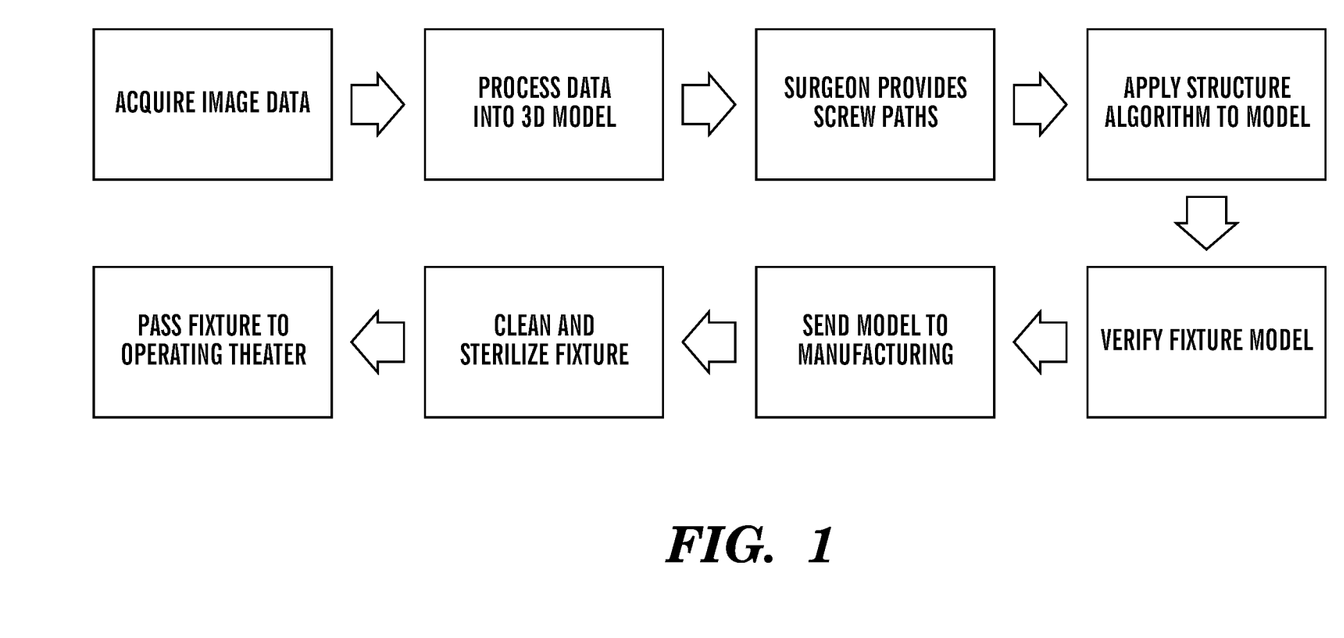
FIG. 1 is a flow chart of a process for spinal fixation according to an embodiment of the present disclosure.

The design of the device is generated based on a template of a predefined geometry applied to a three-dimensional model of the patients' spine. The three-dimensional model can be obtained using any current imaging technique including but not limited to computer tomography (CT) scans, or Magnetic Resonate Imaging (MRI). A technician uses computer-based tools to work with the surgeon to determine the number, location, path, and trajectory of the screws to be placed. The technician can use a computer system to apply a pre-determined format for the fixture to the locations noted by the surgeon. The device is then produced out of the appropriate material through the use of additive manufacturing techniques. Final cleaning and sterilization can be performed before the device is passed to the operating theater for implantation. FIG. 1 demonstrates an embodiment of the process as a flow chart.

Figure 4A:
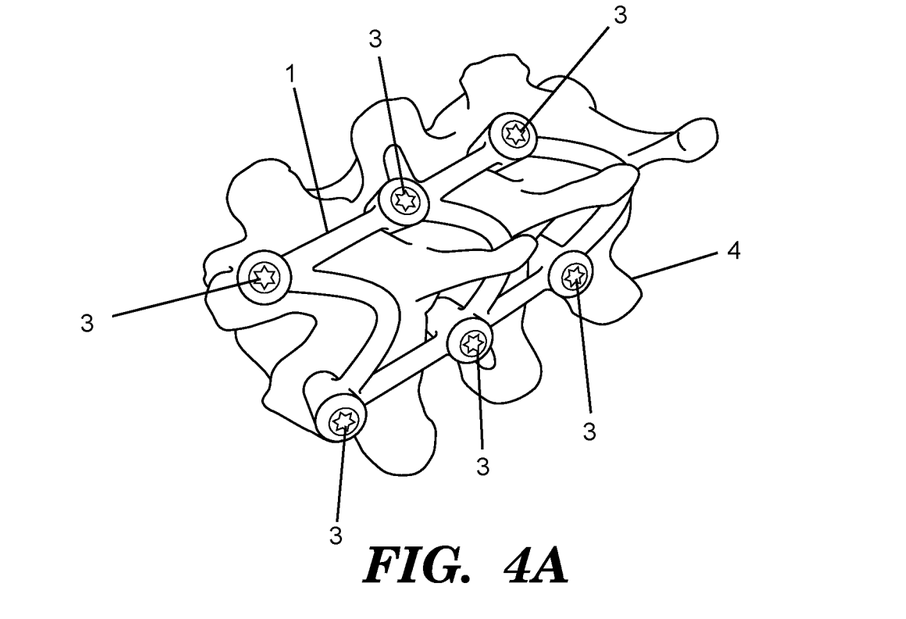
FIG. 4A is a perspective view of a 3D printed implant with pedicle screws and FIG. 4B is a perspective view of a 3D printed implant without screws in accordance with an embodiment of the present disclosure.
Figure 4B:
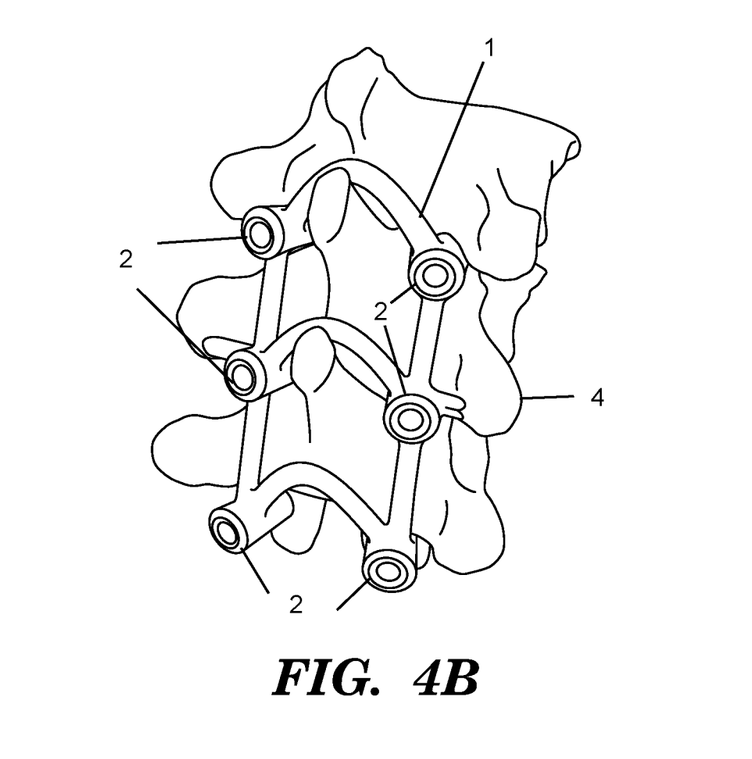
Figure 5:
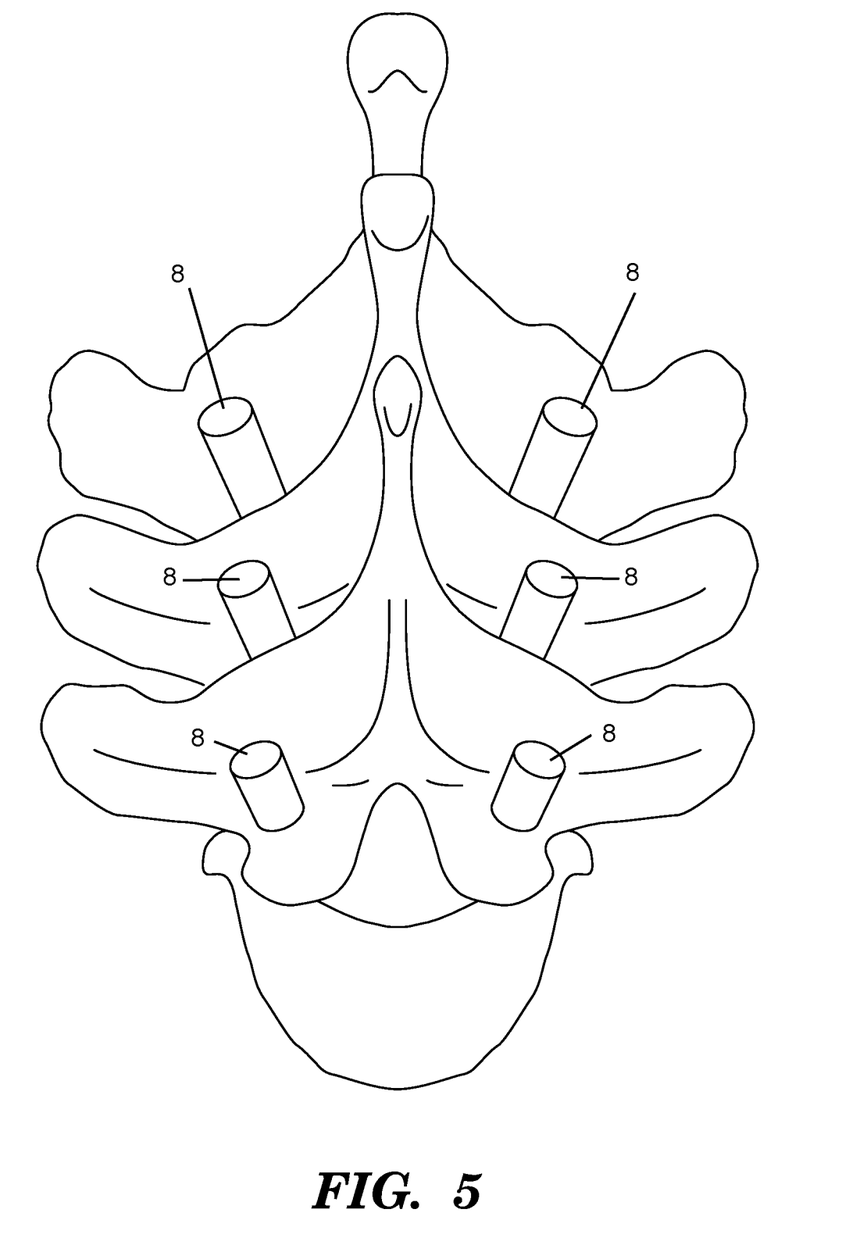
FIG. 5 is a digital image of an affected segment of a patient's spine showing specific screw paths in accordance with an embodiment of the present disclosure.
Figure 6:
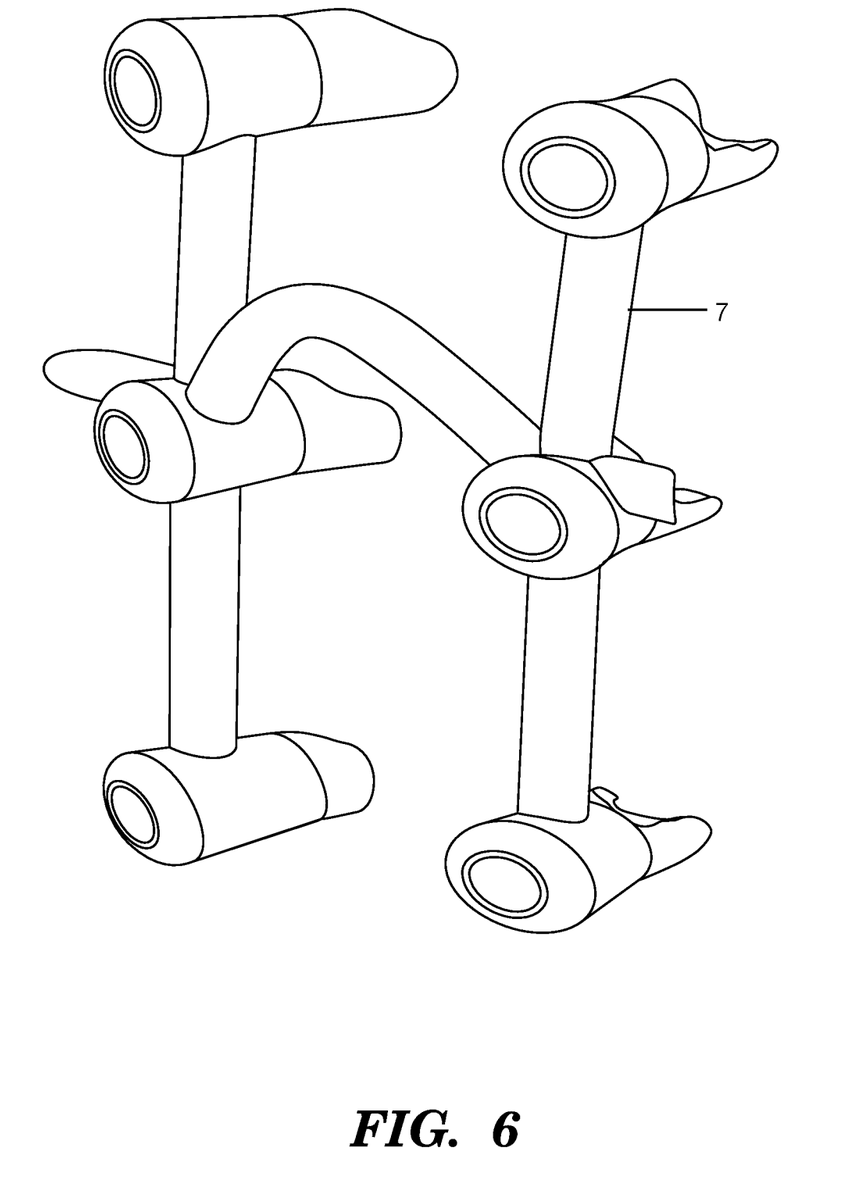
FIG. 6 is a 3D digital image of a template model for the fixture in accordance with an embodiment of the present disclosure.
Figure 7:
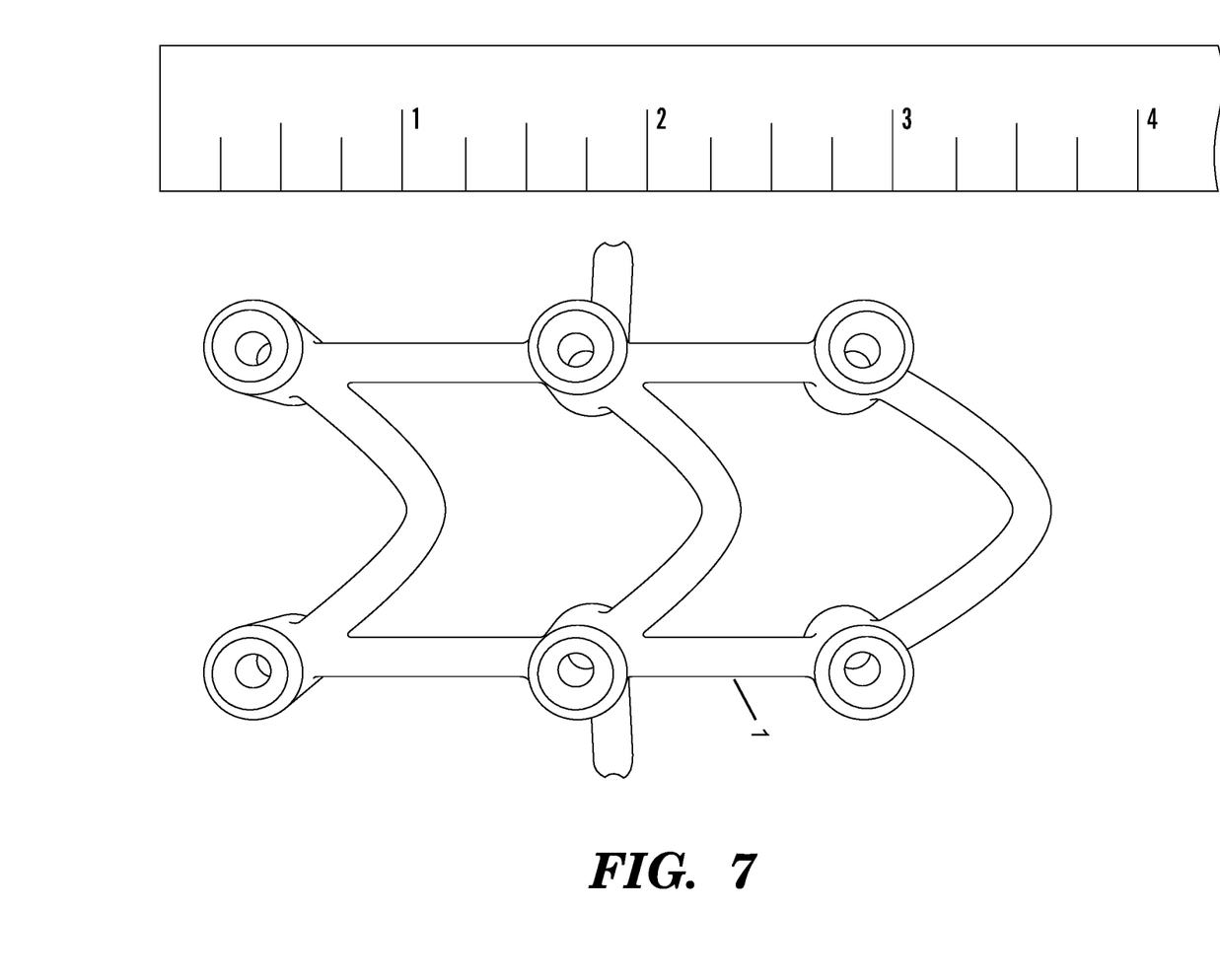
FIG. 7 is a photograph of an additive manufactured fixture in accordance with an embodiment of the present disclosure.
Figure 8:
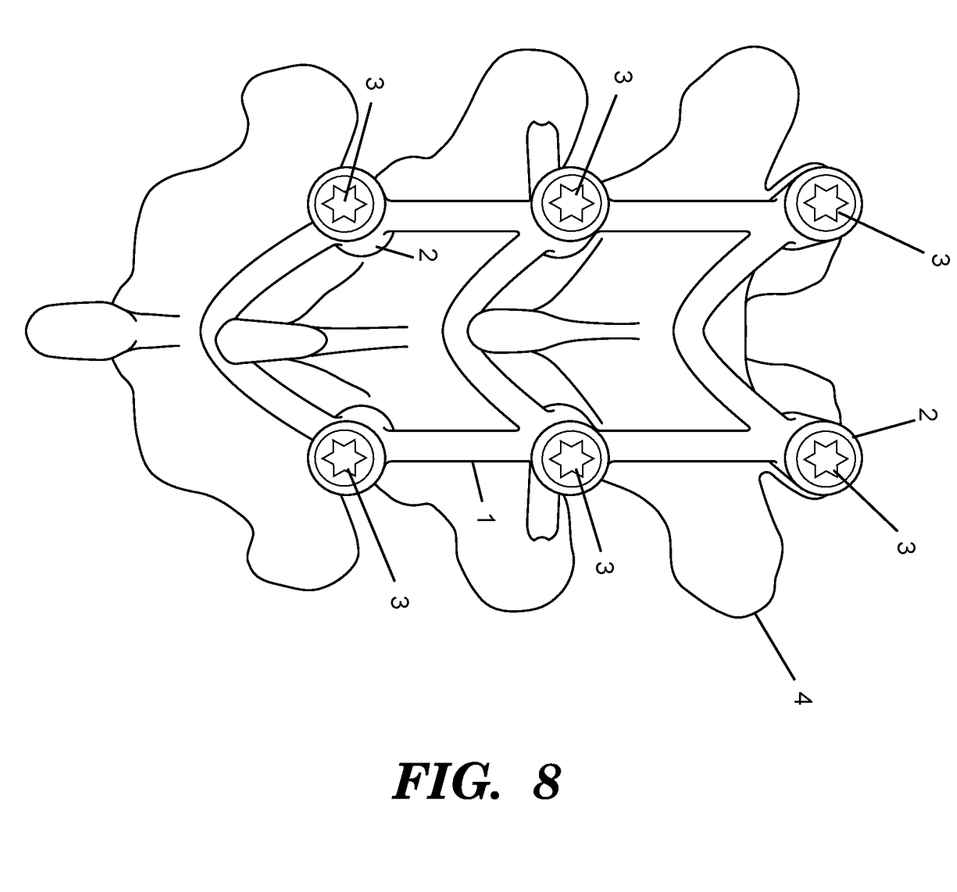
FIG. 8 is a photograph of the fixture of FIG. 7 screwed into a model of a section of spine.

An embodiment includes a method wherein a patient, for example, presents with a fracture in the thoracic $10^{th}$ vertebra, after consult with a neurosurgeon it is decided that spinal fixation is required. The patient is moved to radiology and has a CT scan performed on the affected segment of the spine. A technician generates a 3D model of the spine based off of image data. The surgeon joins the technician and a set of specific screw entry points and trajectories are selected to best treat the patients' condition. The technician uses software to make a digital template 7, as shown in FIG. 6, for the fixture and modify the template to fit the selected screw paths 8, as shown in FIG. 5. The finished digital template is then inspected by the technician and sent to a device for additive manufacturing to make the fixture 1, as shown in FIG. 7. When finished the fixture is cleaned, prepared, and sterlized before sending to the operating theater. After dissection by the surgeon the fixture is located on the spine. The surgeon then uses a standard surgical drill passing through each screw passage 2 (guide) in the fixture 1, as shown in FIG. 4B. Once screw trajectory is created through the screw passage 2, a standard surgical screw 3 with pre-determined dimensions is placed through the screw passage in the fixture until the fixture boss is tightly seated to the vertebra 4. This is repeated for each screw passage in the fixture 1, as shown in FIGS. 4A and 8. When completed the surgeon closes the incision, leaving the fixture in place to stabilize and support the affected vertebra.

Primary uses of the technology include spinal fusion where indications include mechanical low back pain, such as a) treatment of lower back pain due to degenerative disc disease, where a disc collapses over a period of time and patients having failed a conservative treatment, surgical treatment is pursued; b) degenerative spondylolisthesis, and isthmic spondylolisthesis, which occurs when a vertebra slips forward with respect to the lower adjacent vertebra, due to age related changes or defect in bone; and c) treatment of fractures to the vertebra resulting in instability requiring surgical stabilization, as well as, spinal fusion where indications include neurological symptoms, such as a) treatment of spinal stenosis, a narrowing of the passage(s) containing the spinal nerves where spine requires stabilization after decompression of the neural structures; and b) treatment of spinal tumors, which can occur at various locations and may require removal, and tumor resection can cause severe instability in the spine requiring stabilization.

Expanded uses include: spinal fusion where indications include gross malalignment, such as a) treatment of scoliosis, or disabling sideways curvature at multiple levels of the spine, which could be genetic or related to unknown cause; and b) treatment of kyphosis, or incorrect forward curvature in multiple levels of the spine, which like scoliosis, could be genetic or related to unknown cause.

Additional future uses can include the application of the technique and a similar fixture to any orthopedic surgical implant where a complex or non-common fracture is present. The technique and a similar fixture can also be used where there is fear or high probability of malreduction.

Unlike intra-operative navigation the fixture is prepared before the start of the operation, resulting in a faster procedure that requires no additional support of technicians in the operating room. The fixture also removes the uncertainty of free hand placement techniques, and intraoperative navigation by providing a restricted and pre-defined path for the screws. Due to the certainty of placement the need for most secondary modalities will be removed, and can be replaced with fluoroscopy, which requires no specialized equipment and the associated costs. Additionally the need for complex pedicle screws, custom bending jigs for rods, and custom tooling for insertion, can be replaced by standard orthopedic screws.

Of the spinal implants that are produced through the use of both additive manufacturing or rapid prototyping, and patient specific customization, none offer a system that can be used to locate pedicle screw positions, and then remain attached to the spine as a supporting fixture.

Most researchers are concerned with outmoding the use of manual placement, developing custom fixtures, or developing assistive drill guides. While all of these technologies share common references, i.e., the use of computer-generated models based on patient scans, none of the research tends to extend outside of its sphere of interest. This results in solutions that are generated in a silo approach, each seeking to further its own solution vector.

This invention presents a singular solution that provides a device that acts as both a guide for proper screw placement in the pedicles of a vertebra, and then remains as the supporting superstructure implant within the spine. This reduces the complexity, time, and net cost for the surgical procedure.

The device contains the minimal required cross section and geometry to allow for both placement, and support, both in the lateral and transverse planes. This results in a minimum amount of foreign material in the body reducing healing time as well as the chances of postoperative complications.

The device contains unique locating features for location on the transverse process, which aids in correct placement as well as additional stability in the device. The device is simple in use requiring no additional personnel, or advanced technology during the procedure. The use of this invention can greatly decrease time spent in the operating theater thus resulting in a procedure that is safer and less expensive for the patient and hospital. This device provides a design that can be produced out of a range of biocompatible materials. The device can be adapted to any region of the spine, and can be expanded to include any number of levels. The device allows for a less complicated screw design and less complicated insertion tools.

Standard insertion tools, screws, drills, and drill guides are used. These items can be found in common surgical tools in orthopedic fixation kits. These tools can be used with little to no design modification. The device does not require additional surgical opening, or any additional scanning procedures outside of those typically prescribed.

Potential Commercial Uses: This invention is a procedure/process that is the primary product for spinal fusion. To this end the number of surgical approaches and techniques is limited only by the number of cases where a posterior approach is indicated, and thus this product is determined to be the preferred modality. This would be beneficial to a medical device company as there are currently in excess of 1 million spinal fixation procedures performed yearly. In addition many major medical device manufacturing companies have already invested in additive manufacturing equipment and technologies. This would a highly complementary component to their current technology and product base, and could make use of much of the existing technology already available.

This invention would be in direct competition with existing screw and rod style fixation systems, and would likely outmode these systems. In addition there are a number of expensive alternative systems that use image and robotic guidance to drill the initial placement holes for the pedicle screws. This would likely be a large competitor as push towards the more expensive and sophisticated technology has occurred in the absence of a successful all in one solution such as this product. There are other modalities for spinal fusion that would not be replaced by this technology, as the indications for such fixtures are different.

The potential to leverage additive manufacturing (3D-Printing) technology to create customizable implant solutions for a procedure called Anterior Lumbar Interbody Fusion. This procedure is used to treat patients who suffer from compression of the lower vertebrae, causing chronic pain and mobility issues. Currently, surgical treatment relies on the insertion of mass-produced, pre-fabricated implants between vertebrae to correct the compressed spacing, and hand-placed screws to hold an alignment plate in place.

The current innovative design seeks to reduce the risks by simplifying the placement of screws that hold everything in place. Rather than relying only on the steady hand of a surgeon, we use the structural implant itself as a drill guide for precise screw placement. The challenge in this design is that each patient's geometry—the spacing of their vertebrae, the angle of their pedicles—is unique and different; a stock, mass-produced implant thus simply would not work for everybody. However, we were able to take a magnetic resonance image (MRI) of a patient's spine and translate its geometric data into a numerical point cloud, which could then be interpreted by computer aided design (CAD) software. From this data, a 3D model of a geometrically-specific implant was built. It was readily apparent that intricate geometry of this model would be nearly impossible (and certainly expensive) to accomplish using traditional manufacturing techniques. Using a type of 3D-printing called direct metal laser sintering (DMLS), however, we could print the implant in a matter of hours.

Initial parts have been printed in stainless steel in order to minimize cost during the proof-of-concept stage. However, advanced 3D-printing technology will allow final parts to be printed in standard medical-grade titanium. Titanium allows for stronger and lighter implants with complex geometry, and enables better imaging results in follow-up assessment of implant performance. The porous properties that can be achieved with 3D printed titanium also mimic the spongy cancellous bone ordinarily used in grafting procedures; an advanced means of encouraging bone in-growth to further support the fusion structure.

Using MRI data to build customized spinal implants captures unique patient geometry that may improve final fit and function. Beyond this, simplified screw insertion guides tailored to the patient's unique geometry reduces the risks of structural damage or injury resulting from misplacement, ultimately offering improved outcomes to the patient. In addition, the ability to create implants in-house and on-demand at the provider-level can reduce the material and storage costs of maintaining a stock of prefabricated implant parts.

Although translation of MM data into a usable CAD file is both time- and labor-intensive, advancements in both software translation and 3D-printing technology may be enabled, potentially reducing the turnaround time from weeks to days or even hours. Market implementation is challenging, but also promising. The use of pedicle screws to support spinal fusion has been FDA approved for over a decade, and although there are several steps to achieve approval for a new device, similar systems were granted premarket approval in 2012 and cleared for full-scale use by 2016.

Figure 9A:
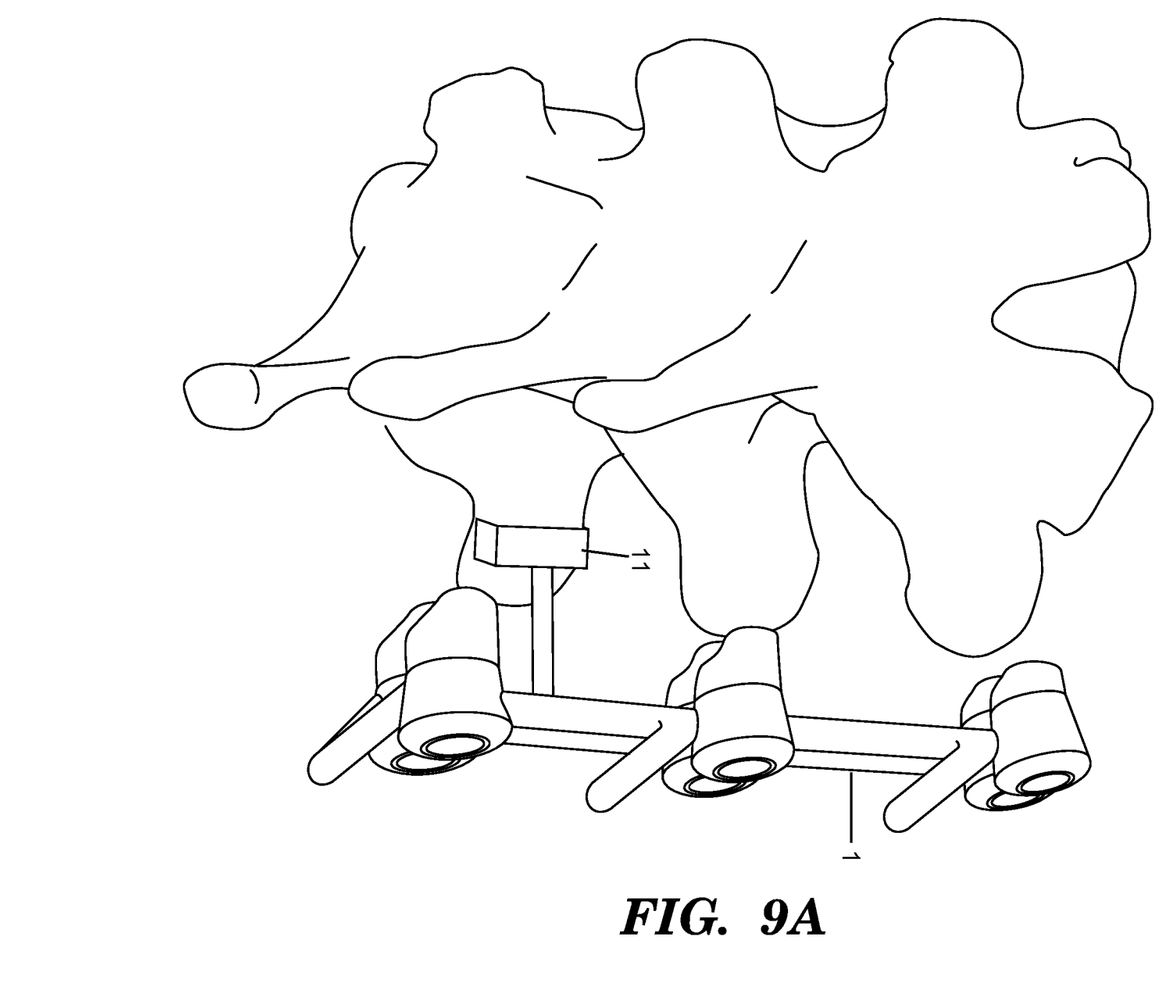
FIGS. 9A-E illustrates a surgical workflow in accordance with an embodiment of the present disclosure.
Figure 9B:
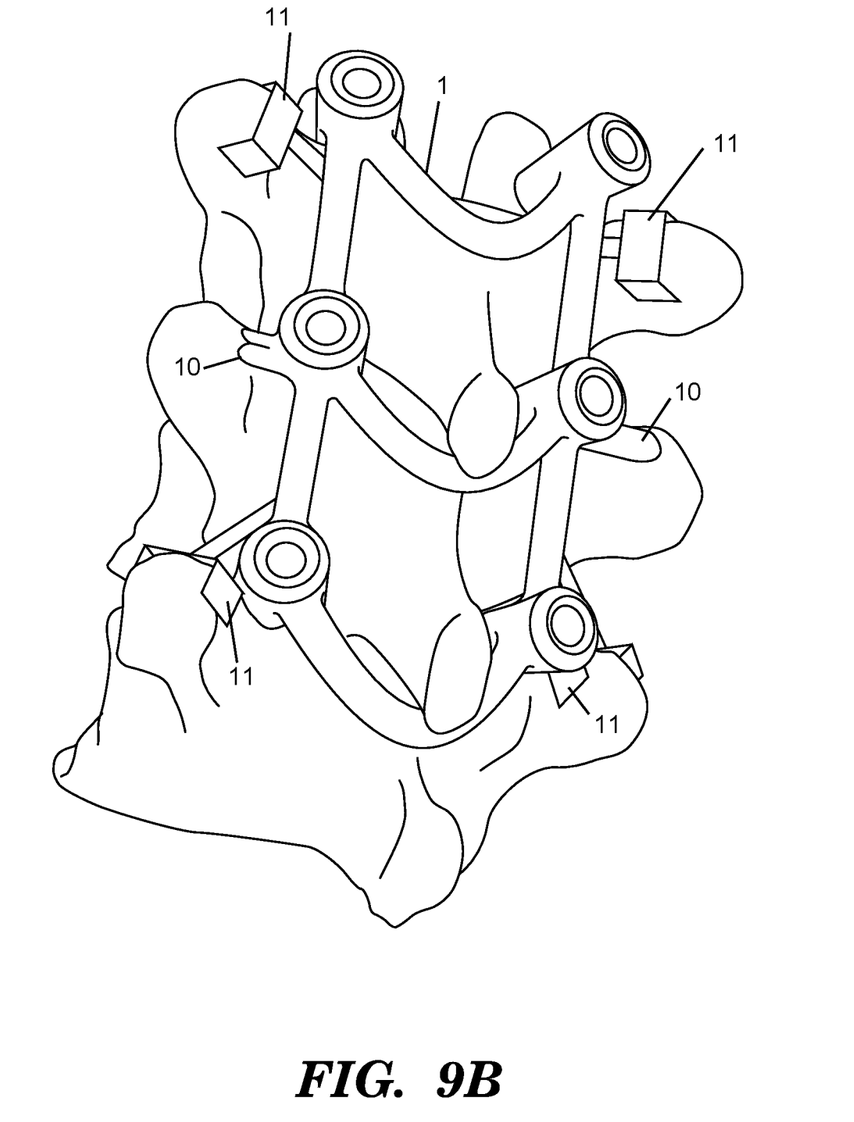

A surgical workflow which includes self-aligning details is shown in FIGS. 9A-E. The surgical exposure is done in the conventional way with exposure of the posterior elements of the vertebrae including the transverse processes. Once the surgical exposure has been completed and the bony anatomy exposed, the 3D printed fixture is brought into the surgical field, FIG. 9A. The fixture is then secured onto the spine using the patient-specific anatomy and the self-aligning side bars 10, as shown in FIG. 9B. The self-aligning bars 10 will be sitting against the bony elements including transverse processes in the thoracic spine and articular facets in the lumbar spine. In addition, alternate transverse process clamps 11 on the fixture are used to hook onto the superior aspect of transverse processes of the vertebral body for additional stability. Once the fixture is secured to the spine, then the electric drill is used to drill the screw trajectory into the pedicle through the in-built guides 2 (shown in FIG. 9C) in the fixture. The in-built guides 2 are located and angled based on the chosen entry points and trajectories for placement of the pedicles screws 3 on the digital 3D model.

Once the screw trajectories have been created, additional surgical steps can be performed such as decompression, interbody device placement and scoliosis rotational maneuvers.

If the spine alignment or the distance between the pedicle changes after the decompression or other secondary procedure such as scoliosis correction, then various methods can be taken. The 3D manufactured fixture can be bent/rotated according to the spine alignment to fit in the screw trajectories created before the correction in the spine alignment. If the 3D manufactured fixture cannot be aligned with the some of the screw trajectories created before, additional guides 13 with polyaxial heads (shown in FIGS. 9C and 9D) can be attached onto the 3D manufactured fixture as necessary. The screws can then be passed through the guides with polyaxial heads into the trajectories created before to hold the 3D manufactured fixture onto the spine.

Figure 9C:
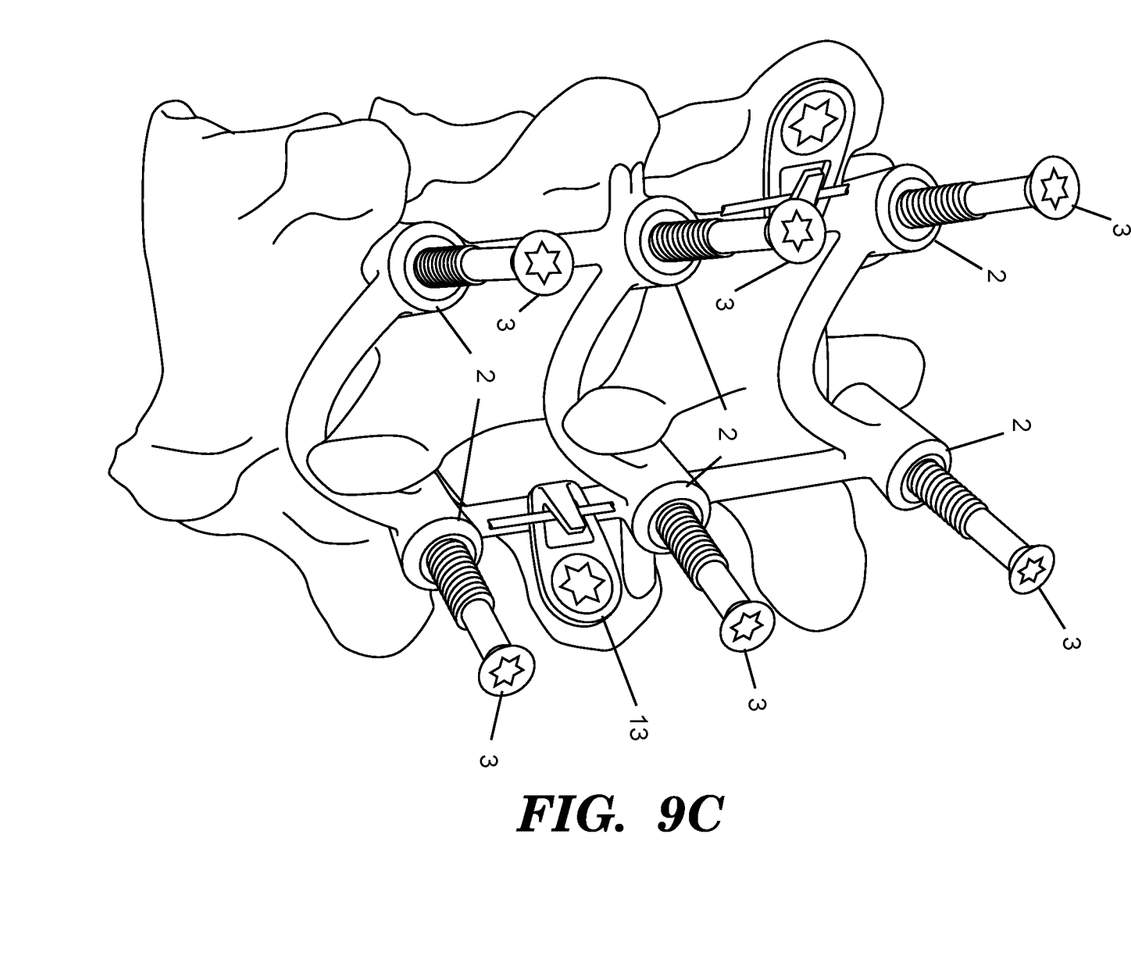
Figure 9D:
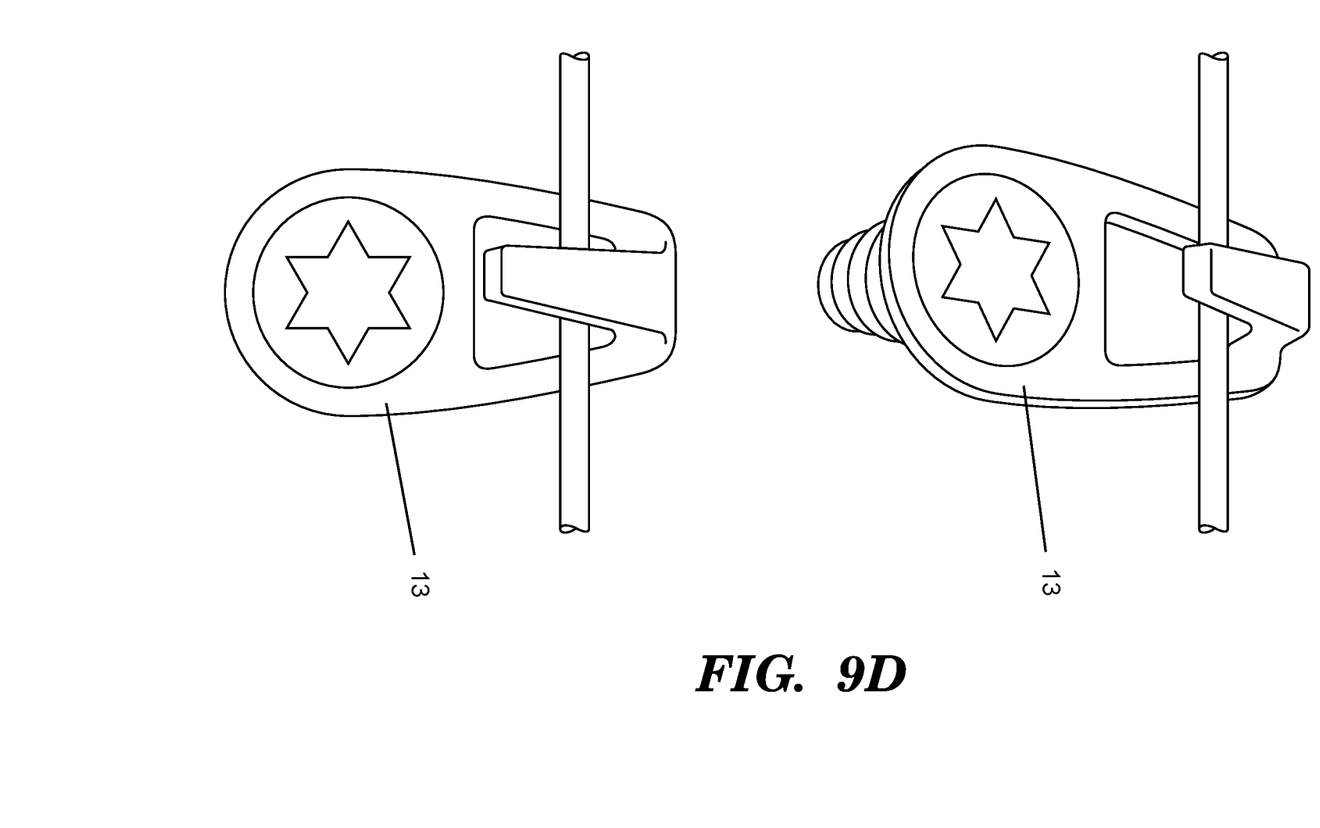
Figure 9E:
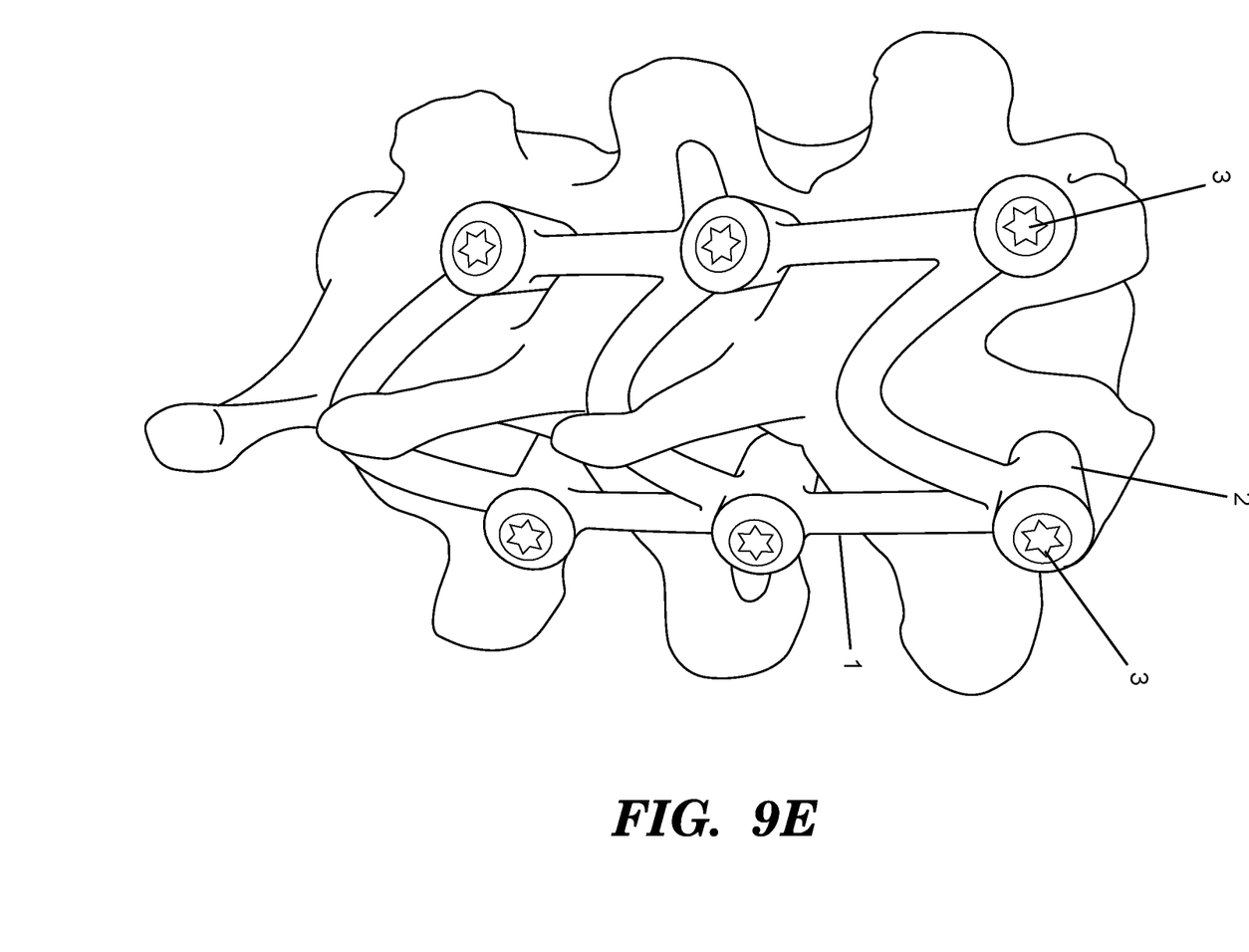

The fixture is then brought again into the surgical field and finally attached to the spine using the screws 3 through the trajectories created before, as shown in FIG. 9E.

The surgical steps mentioned above can be trialed on the 3D spine template using the 3D fixture prior to surgery to judge the need to rotate the fixture or where additional guides would need to be attached. As the fixture will be based on pre-operative planning and specific for the patient, this would eliminate the need to determine the length and to cut the rods which is another cumbersome and time consuming process during the surgeries.

Based on the CT scan, the 3D digital model will be created. The spine is curved and generally the CT scans are acquired with respect to the body axis which is a straight line, however the sections can be acquired in the line of the pedicles (parallel to the pedicles) instead of at an angle using the standard PACS (radiology) software. This has to be requested sometimes from the CT technician.

The entry point, point in the center of the pedicle and distal point in the vertebral body will be selected in the digital model on the computer working station by the technician in discussion with the surgeon.

The pedicle screw size and trajectory will be decided on the 3D digital model. 3D digital model is currently being used in the navigation and robotics technology in spine instrumentation to choose the screw size and trajectory. The template of the 3D digital model will be created and the plan can be tested on the template for complex surgeries such as scoliosis.

The 3D digital fixture will be manufactured based on the chosen screw entry points and trajectory on the 3D digital model of the spine. The digital template of the fixture will then be 3D printed and likewise the digital data will be transferred over to make a metallic titanium replica as an implantable fixture.

The fixture will be sterilized and passed on during the surgery. The fixture will have the self-alignment side bars 10 as shown in FIG. 9B which will be gently tapped into surrounding bone to prevent rotation and migration of the fixture. The fixture will have the in-built guides 2 (as shown in FIG. 9C) through which the screw trajectories will be drilled and they will accommodate the pre-determined screw sizes. The outer diameter of these guides will be uniform to accept the extensions if needed which can be attached to guides to prevent mis-angulation of the drill.

In addition to the self-alignment side bars, the fixture can have the alternate transverse process clamps to hook onto the transverse processes to provide additional stability to provide immobilization. Once the screw trajectories have been prepared, the transverse process clamps can be removed. It will be important to remove the transverse process clamps before fixation of the fixture in case the fixture has to be removed later on in future which could be needed due to different reasons.

The current surgical planning platforms which can provide 3D digital imaging and planning data such as Mazor robotics, iPlan from Brainlab currently in use, could be integrated with the process of designing and building the 3D spine and 3D fixture template and final 3D fixture.

The invention will be further illustrated with reference to the following specific examples. It is understood that these examples are given by way of illustration and are not meant to limit the disclosure or the claims to follow.

Example: A prototype device was generated based on anonymous medical donor data of a spine. The thoracic 8,9,10 vertebra were selected for a test section. The prototype was generated in SolidWorks along with the 3-dimensional model of the selected vertebra. For testing purposes, 15 sets of the three level donor vertebra were produced using an Objet30 pro 3D printer in the Mechanical and Manufacturing Engineering Technology department. A prototype of the device was also generated using the same equipment and plastic material.

The testing would be performed by placing a vertebra section into a metal stand that would fix the rotation and translation of the vertebra, while only exposing the region of the spine that would be available to the surgeon. Once locked in the stand, the prototype fixture would be placed on the spine, and a suite of standard surgical orthopedic tools will be used to first drill clearance holes and then place screws into the spine. Once completed the section would be checked for any breaches, and if present the breach type and quality would be graded, and noted. A total of 36 screws will be placed across 5 test sections. All screws placed will use the same fixture, tools and procedure, with only the only difference being a new test section. This will be done to reduce the variability and additional factors within the test. At the conclusion the number of and quality of breaches will be compared to those for a standard hand placement procedure. A series of initial prototypes were produced in the CAST department's additive manufacturing lab. These initial prototypes were produced for validation of general fixture location, and were produced from a UV cure polymer on an Objet30 pro 3D printer. A second model of the fixture was produced to verify the fitment and validity of selective laser sintering to produce the fixture. This component was produced by the Center for Integrated Manufacturing Studies at RIT and was created from nylon. The final prototype that will be used for testing was produced by the Center for Integrated Manufacturing Studies at RIT. This variant of the prototype was produced from PH-17 stainless steel on a 3D systems selective laser sintering device.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for spinal fixation comprising:
    scanning an affected segment of the spine of a patient in need of spinal fixation to generate image data;
    generating a 3D model of the spine from the image data;
    selecting a set of screw paths in the 3D model for attachment of an implant to the affected segment of the spine;
    generating a 3D digital template of a combination screw guide fixture and implant comprising screw guides corresponding to the set of selected screw paths and at least one self-alignment bar comprising a vertebra mating surface;
    making the combination screw guide fixture and implant from the 3D digital template by additive manufacturing;
    locating the combination screw guide fixture and implant on the affected segment of the spine aligning the screw guides with the set of selected screw paths and contacting the at least one self-alignment bar vertebra mating surface with the vertebra;
    drilling a hole in the vertebra corresponding to each screw path in the set of selected screw paths using the screw guides;
    placing a surgical screw through each screw guide into the corresponding hole in the vertebra; and
    tightening each surgical screw until the combination screw guide fixture and implant is tightly seated to the vertebra.

2. The method of claim 1, further comprising:
    attaching a transverse process clamp onto a transverse process of the vertebra and a side rod prior to drilling a hole in the vertebra; and
    removing the attached transverse process clamp after drilling the holes in the vertebra.

3. The method of claim 1, further comprising:
    attaching an extension sleeve to the screw guide prior to drilling a hole.

4. The method of claim 1, wherein the combination screw guide fixture and implant comprises, a left-side rod; a right-side rod; and a plurality of interconnecting bars connecting the left-side rod to the right-side rod, the left-side rod comprising a self-alignment bar comprising a vertebra mating surface and extending out from the left-side rod and a plurality of screw passages corresponding to a first portion of the screw guides suitable for accepting screws capable of tightening the combination screw guide fixture and implant to vertebra, the right-side rod comprising a self-alignment bar comprising a vertebra mating surface and extending out from the right-side rod and a plurality of screw passages corresponding to a second portion of the screw guides suitable for accepting screws capable of tightening the combination screw guide fixture and implant to vertebra.

5. The method of claim 1, wherein the screw guides comprise multiple pairs of screw guides and each pair of the multiple pairs of screw guides is attached to separate vertebra.

6. A customized patient-specific spinal fixation combination screw guide fixture and implant comprising:
   an additive manufacturing-made spinal fixation combination screw guide fixture and implant, comprising a left-side rod; a right-side rod; and a plurality of interconnecting bars connecting the left-side rod to the right-side rod, the left-side rod comprising a at least two self-alignment bars comprising a corresponding vertebra mating surface and extending out from the left-side rod and a plurality of screw passages suitable for accepting screws capable of tightening the combination screw guide fixture and implant to vertebra, the right-side rod comprising at least two self-alignment bars comprising a corresponding vertebra mating surface and extending out from the right-side rod and a plurality of screw passages suitable for accepting screws capable of tightening the combination screw guide fixture and implant to vertebra which combination screw guide fixture and implant remains screwed on the vertebra after spinal fixation, wherein one of multiple screw passages of the left-side rod plurality of screw passages are paired with a corresponding one of multiple screw passages of the right-side rod plurality of screw passages by connection to one of the plurality of interconnecting bars.

7. The product of claim 6, wherein the combination screw guide fixture and implant comprises at least 2 paired screw passages.

8. The product of claim 6, wherein the combination screw guide fixture and implant comprises 3 paired screw passages.

9. The product of claim 6, wherein each screw passage of the left-side rod plurality of screw passages is paired with a corresponding one of the right-side rod plurality of screw passages by connection to one of the plurality of interconnecting bars.

\* \* \* \* \*